(12) United States Patent
Schwartz et al.

(10) Patent No.: US 6,340,567 B1
(45) Date of Patent: *Jan. 22, 2002

(54) GENOMICS VIA OPTICAL MAPPING WITH ORDERED RESTRICTION MAPS

(75) Inventors: David C. Schwartz, New York; Bhubaneswar Mishra, Great Neck; Thomas S. Anantharaman, Carmel, all of NY (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/678,002

(22) Filed: Oct. 3, 2000

Related U.S. Application Data

(63) Continuation of application No. 08/887,971, filed on Jul. 2, 1997, now Pat. No. 6,174,671.

(51) Int. Cl.[7] .......................... C12Q 1/00; C12Q 1/68; C12P 21/06; C12P 1/00; G01N 21/00

(52) U.S. Cl. ................ 435/6; 435/69.1; 435/4; 435/41; 422/50; 422/55; 422/99

(58) Field of Search ........................ 435/6, 69.5, 4, 435/41; 422/50, 55, 99

(56) References Cited

U.S. PATENT DOCUMENTS 6,174,671 B1 * 1/2001 Anantharaman et al. ....... 435/6

* cited by examiner

*Primary Examiner*—Jezia Riley
(74) *Attorney, Agent, or Firm*—Pennie & Edmonds LLP

(57) ABSTRACT

A method of producing high-resolution, high-accuracy ordered restriction maps based on data created from the images of populations of individual DNA molecules (clones) digested by restriction enzymes. Detailed modeling and a statistical algorithm, along with an interactive algorithm based on dynamic programming and a heuristic method employing branch-and-bound procedures, are used to find the most likely true restriction map, based on experimental data.

19 Claims, 4 Drawing Sheets

GENOMICS VIA OPTICAL MAPPING WITH ORDERED RESTRICTION MAPS

CROSS-REFERENCE TO RELATED APPLICATIONS

This is a continuation of Application No. 08/887,971, filed Jul. 2, 1997 now U.S. Pat. No. 6,174,671.

BACKGROUND OF THE INVENTION

This invention relates to the construction of ordered restriction maps and, more particularly, to a method capable of producing high-resolution, high-accuracy maps rapidly and in a scalable manner.

Optical mapping is a single molecule methodology for the rapid production of ordered restriction maps from individual DNA molecules. Ordered restriction maps are constructed by using fluorescence microscopy to visualize restriction endonuclease cutting events on individual fluorochrome-stained DNA molecules. Restriction enzyme cleavage sites are visible as gaps that appear flanking the relaxed DNA fragments (pieces of molecules between two consecutive cleavages). Relative fluorescence intensity (measuring the amount of fluorochrome binding to the restriction fragment) or apparent length measurements (along a well-defined "backbone" spanning the restriction fragment) have proven to provide accurate size-estimates of the restriction fragment and have been used to construct the final restriction map.

Such a restriction map created from one individual DNA molecule is limited in its accuracy by the resolution of the microscopy, the imaging system (CCD camera, quantization level, etc.), illumination and surface conditions. Furthermore, depending on the digestion rate and the noise inherent to the intensity distribution along the DNA molecule, with some probability one is likely to miss a small fraction of the restriction sites or introduce spurious sites. Additionally, investigators may sometimes (rather infrequently) lack the exact orientation information (whether the left-most restriction site is the first or the last). Thus, given two arbitrary single molecule restriction maps for the same DNA clone obtained this way, the maps are expected to be roughly the same in the following sense—if the maps are "aligned" by first choosing the orientation and then identifying the restrictions sites that differ by small amount, then most of the restrictions sites will appear roughly at the same place in both the maps.

There are two approaches to further improve the accuracy and resolution of the maps: first, improve the chemical and optical processes to minimize the effect of each error source and second, use statistical approaches where the restriction maps of a large number of identical clones are combined to create a high-accuracy restriction map. These two approaches are not mutually exclusive and interesting trade-offs exist that can be exploited fruitfully.

For instance, in the original method, fluorescently-labeled DNA molecules were elongated in a flow of molten agarose containing restriction endonucleases, generated between a cover-slip and a microscope slide, and the resulting cleavage events were recorded by fluorescence microscopy as time-lapse digitized images. The second generation optical mapping approach, which dispensed with agarose and time-lapsed imaging, involves fixing elongated DNA molecules onto positively-charged glass surfaces, thus improving sizing precision as well as throughput for a wide range of cloning vectors (cosmid, bacteriophage, and yeast or bacterial artificial chromosomes (YAC or BAC)). Further improvements have recently come from many sources: development of a simple and reliable procedure to mount large DNA molecules with good molecular extension and minimal breakage; optimization of the surface derivatization, maximizing the range of usable restriction enzymes and retention of small fragments; and development of an open surface digestion format, facilitating access to samples and laying the foundations for automated approaches to mapping large insert clones.

Improvements have also come from powerful statistical tools that process a preliminary collection of single-molecule restriction maps, each one created from an image of a DNA molecule belonging to a pool of identical clones. Such restriction maps are almost identical with small variations resulting from sizing errors, partially digested restriction sites and "false" restriction sites. Such maps can be combined easily in most cases. However, the underlying statistical problem poses many fundamental challenges; for example, the presence of some uncertainty in the alignment of a molecule (both orientation and/or matching in the sites) in conjunction with either false cuts or sizing error is sufficient to make the problem infeasible (NP-complete). M .R. Garey and D. S. Johnson, *Computer and Intractability: A Guide to the Theory of NP-Completeness* (W. H. Freeman and Co., San Francisco 1979).

In spite of the pessimistic results mentioned above, the problem admits efficient algorithms once the structure in the input is exploited. For instance, if the digestion rate is quite high, then by looking at the distribution of the cuts a good guess can be made about the number of cuts and then only the data set with large numbers of cuts can be combined to create the final map. J. Reed, *Optical Mapping*, Ph. D. Thesis, NYU, June 1997 (Expected). Other approaches have used formulations in which one optimizes a cost function and provides heuristics (as the exact optimization problems are often infeasible). In one approach, the optimization problem corresponds to finding weighted cliques; and in another, the formulation corresponds to a 0–1 quadratic programming problem. S. Muthukrishnan and L. Parida. "Towards Constructing Physical Maps by Optical Mapping: An Effective Simple Combinatorial Approach, in *Proceedings First Annual Conference on Computational Molecular Biology*, (RECOMB97), ACM Press, 209–215, 1997). However, these heuristics have only worked on limited sets of data and their efficacy (or approximability) remains unproven.

SUMMARY OF THE INVENTION

In accordance with our invention, we use a carefully constructed prior model of the cuts to infer the best hypothetical model by using Bayes' formula. The solution requires searching over a high-dimensional hypothesis space and is complicated by the fact that the underlying distributions are multimodal. Nevertheless, the search over this space can be accomplished without sacrificing efficiency. Furthermore, one can speed up the algorithm by suitably constraining various parameters in the implementation (but at the loss of accuracy or an increased probability of missing the correct map).

The main ingredients of this method are the following:

A model or hypothesis $\mathcal{H}$, of the map of restriction sites.

A prior distribution of the data in the form of single molecule restriction map (SMRM) vectors:

$Pr[D_j|\mathcal{H}]$.

Assuming pair-wise conditional independence of the SMRM vectors $D_j$, $$Pr[D_j|D_{ji}, \ldots, D_{jm}, \mathcal{H}] = Pr[D_j|\mathcal{H}].$$

Thus, the prior distribution of the entire data set of SMRM vectors becomes $$Pr[\mathcal{D}|\mathcal{H}] = \prod_j^m Pr[D_j|\mathcal{H}],$$

where index j ranges over the data set.

A posterior distribution via Bayes' rule $$Pr[\mathcal{H}|\mathcal{D}] = \frac{Pr[\mathcal{D}|\mathcal{H}]Pr[\mathcal{H}]}{Pr[\mathcal{D}]}$$

Here $\mathbf{P}\mathcal{H}$ is the unconditional distribution of hypothesis $\mathcal{H}$ and $\mathbf{Pr}[D]$ is the unconditional distribution of the data.

Using this formulation, we search over the space of all hypotheses to find the most "plausible" hypothesis $\mathcal{H}$ that maximizes the posterior probability.

The hypotheses $\mathcal{H}$ are modeled by a small number of parameters $\Phi(\mathcal{H})$ (e.g., number of cuts, distributions of the cuts, distributions of the false cuts, etc.). We have prior models for only a few of these parameters (number of cuts), and the other parameters are implicitly assumed to be equi-probable. Thus the model of $\mathbf{Pr}[\mathcal{H}$ is rather simplistic. The unconditional distribution for the data $\mathbf{Pr}[D]$ does not have to be computed at all since it does not affect the choice $\mathcal{H}$. In contrast, we use a very detailed model for the conditional distribution for the data given the chosen parameter values for the hypothesis. One can write the expression for the posterior distribution as:

$$\log(<Pr[\Phi(\mathcal{H})|D]) = = l + Penalty + Bias,$$

where $l \equiv \Sigma_j \log(\mathbf{Pr}[D_j|\Phi(\mathcal{H})]$ is the likelihood function, Penalty=log $\mathbf{Pr}[\hat{\Phi} \mathcal{H}]$ and Bias=$-\log(\mathbf{Pr}[D])$=a constant. In these equations $\Phi(\mathcal{H})$ corresponds to the parameter set describing the hypothesis and $\hat{\Phi}$ $(\mathcal{H}) \subseteq \Phi(\mathcal{H})$ a subset of parameters that have a nontrivial prior model. In the following, we shall often write $\mathcal{H}$ for $\Phi(\mathcal{H})$, when the context creates no ambiguity.

Also, note that the bias term has no effect as it is a constant (independent of the hypothesis), and the penalty term has discernible effect only when the data set is small. Thus, our focus is often on the term l which dominates all other terms in the right hand side.

As we will see the posterior distribution, $\mathbf{Pr}[\mathcal{H}|D]$ is multimodal and the prior distribution $\mathbf{Pr}[D_j\mathcal{H}]$ does not admit a closed form evaluation (as it is dependent on the orientation and alignment with $\mathcal{H}$. Thus, we need to rely on iterative sampling techniques.

Thus the search method to find the most "plausible" hypothesis has two parts: we take a sample hypothesis and locally search for the most plausible hypothesis in its neighborhood using gradient search techniques; we use a global search to generate a set of sample hypotheses and filter out all but the ones that are likely to be near plausible hypotheses.

Our approach using this Bayesian scheme enjoys many advantages:

One obtains the best possible estimate of the map given the data, subject only to the comprehensiveness of the model $\Phi(\mathcal{H})$ used.

For a comprehensive model $\mathcal{H}$ estimates of $\Phi(\mathcal{H})$ are unbiased and errors converge asymptotically to zero as data size increases.

Additional sources of error can be modeled simply by adding parameters to $\Phi(\mathcal{H})$.

Estimates of the errors in the result can be computed in a straightforward manner.

The algorithm provides an easy way to compute a quality measure.

DESCRIPTION OF THE DRAWINGS

These and other objects, features, and elements of the invention will be more readily apparent from the following Description of the Preferred Embodiments of the invention in which.

DESCRIPTION OF THE PREFERRED EMBODIMENTS

This description has several parts. In part A, we describe the restriction map model and formulate the underlying algorithmic problems. In part B, we describe a statistical model for the problem based on assumptions on the distributions of the bases in DNA and the properties of the chemical processes involved in optical mapping. These models are then used, in part C, to describe a probabilistic local search algorithm with good average time complexity. Part D describes an update algorithm which is used in conjunction with the local search algorithm to improve computational efficiency. Part E describes the global search algorithm, and how it is made less computationally expensive through the use of a branch and bound algorithn. Finally, part F describes the quality measure used to determine the best map.

Figure 1:
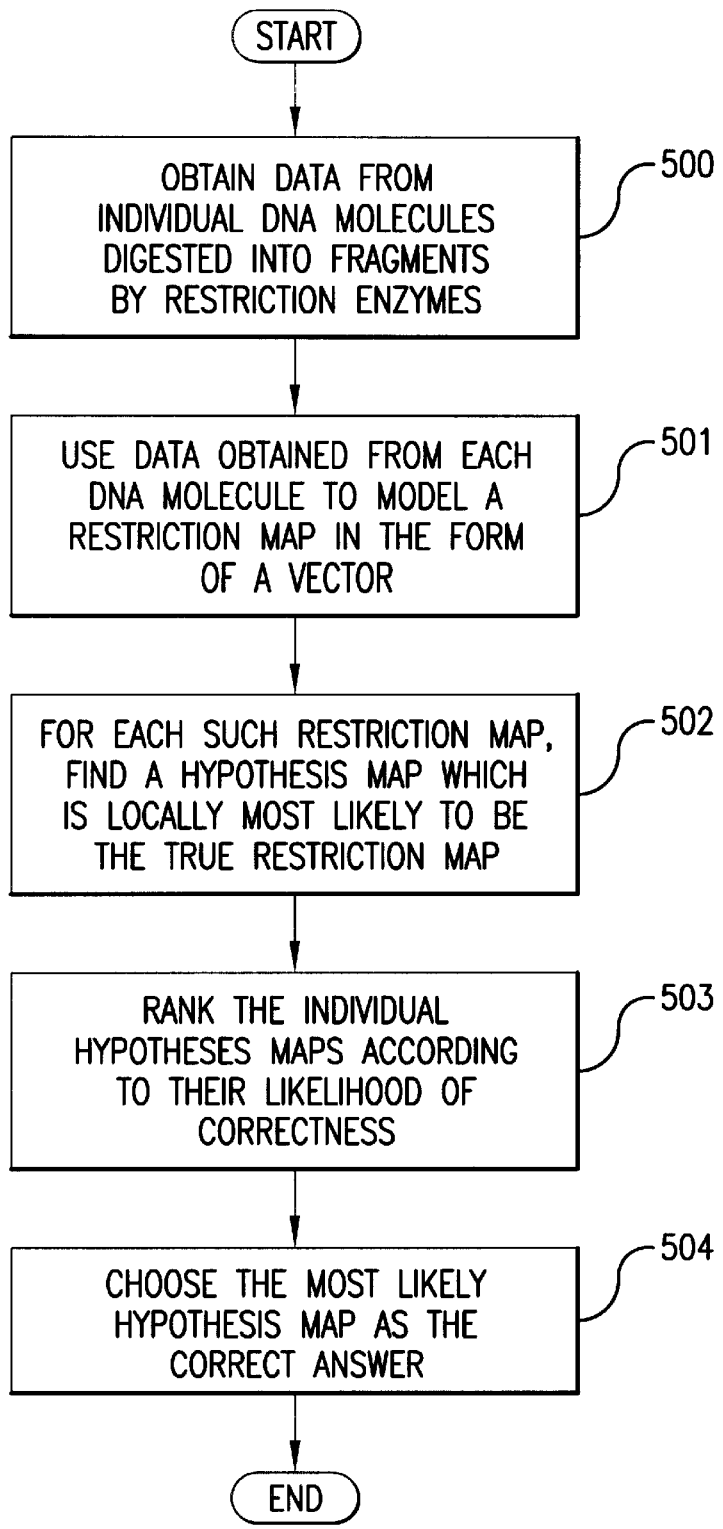
FIGS. 1 and 2 depict in schematic form the global and local searches, respectively.

FIG. 1 illustrates the global search strategy used in the method of the invention. Initially, data is obtained from individual DNA molecules which have been digested into fragments by restriction enzymes (Step 500, FIG. 1). The data (cut sites) is then used to model a restriction map as a vector, for each molecule (Step 501, FIG. 1). Next, for each restriction map, a hypothesis map which is locally most likely to be the true restriction map is found (Step 502, FIG. 1). After the individual locally likely hypotheses are ranked according to their likelihood of correctness (Step 503, FIG. 1), the most likely hypothesis is chosen as the correct, or best, answer (Step 504, FIG. 1).

Figure 2:
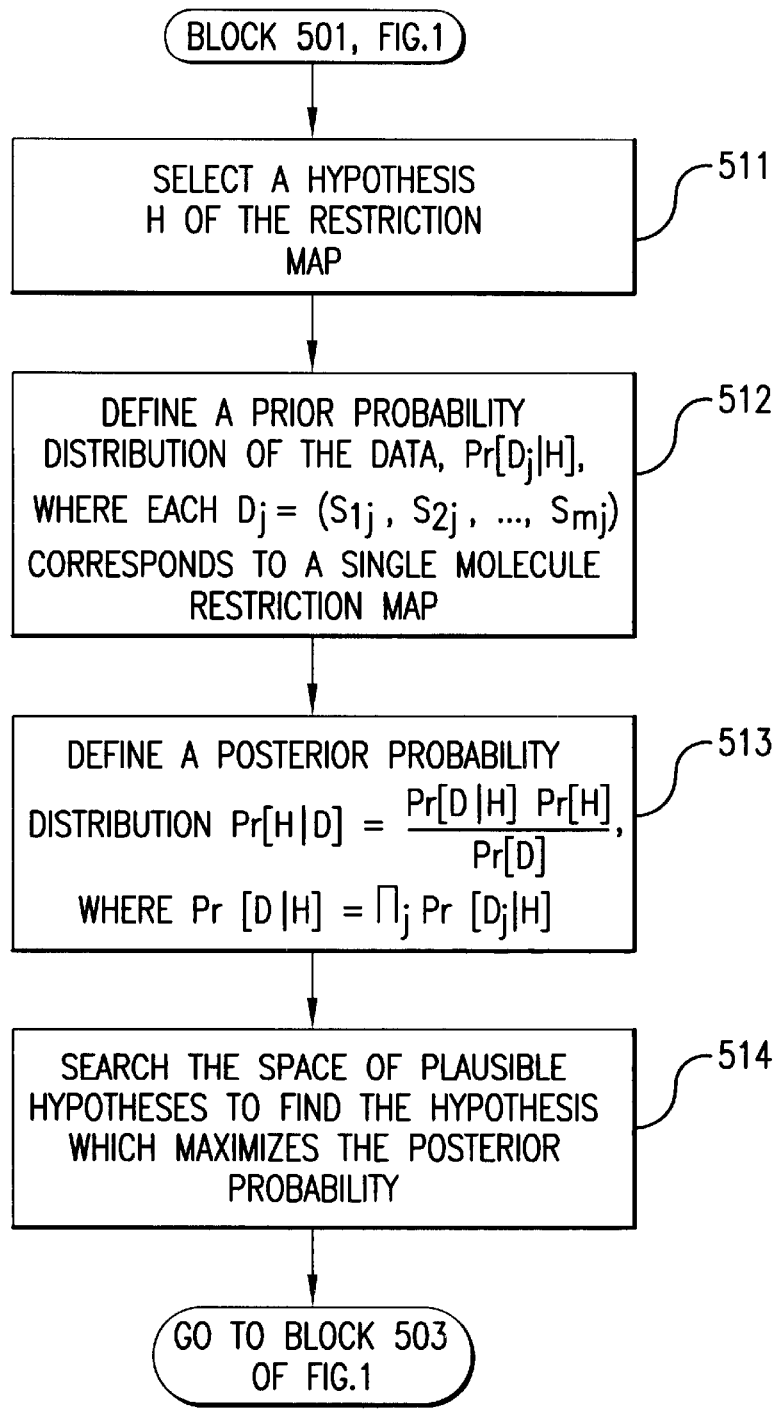

FIG. 2 illustrates a method of searching for the locally most likely hypotheses (Step 502, FIG. 1) wherein a Bayesian approach is used. A. P. Dempster, N. M. Laird and D. B. Rubin, "Maximum Likelihood from Incomplete Data via the EM Algorithm," *J. Roy. Stat. Soc.*, 39(1):1–38, 1977; U. Grenander and M. I. Miller, "Representations of Knowledge in Complex Systems (with discussions), " *J. Roy. Stat.* Soc. B.,56:549–603. After a hypothesis H of the restriction map is selected (Step 511, FIG. 2), a prior probability distribution is defined (Step 512, FIG. 2). A posterior probability distribution is then defined (Step 513, FIG. 2), which is then used to search the space of plausible hypotheses to find the hypothesis which is most likely to be correct (that is, the hypothesis which maximizes the posterior probability distribution (Step 514, FIG. 2).

A. Restriction Map Model

Our problem can be formulated as follows. Assuming that all individual single-molecule restriction maps correspond to the same clone, and that the imaging algorithm can only provide the fragment size estimates that are scaled by some unknown scale factor, we represent a single molecule restriction map (SMRM) by a vector with ordered set of rational numbers on the open unit interval $(0,1)$:

$$D_j = (s_{1j}, s_{2j}, \ldots, s_{M_j j}), \ 0 < s_{1j} < s_{2j} < \ldots < s_{M_j j} < 1, \ s_{ij} \in \mathbf{Q}$$

Given a rational number $s \in (0,1)$, its reflection is denoted by $s^R = 1 - s^-$. Similarly, by $D_j^R$, we denote the vector $$D_j^R = (s_{M_j j}^R, \ldots, s_{2j}^R, s_{1j}^R).$$

Note that if the entries of $D_j$ are ordered and belong to the open unit interval, so do $D_j + c$ and $D_j^R$ provided that c is appropriately constrained.

Figure 3:
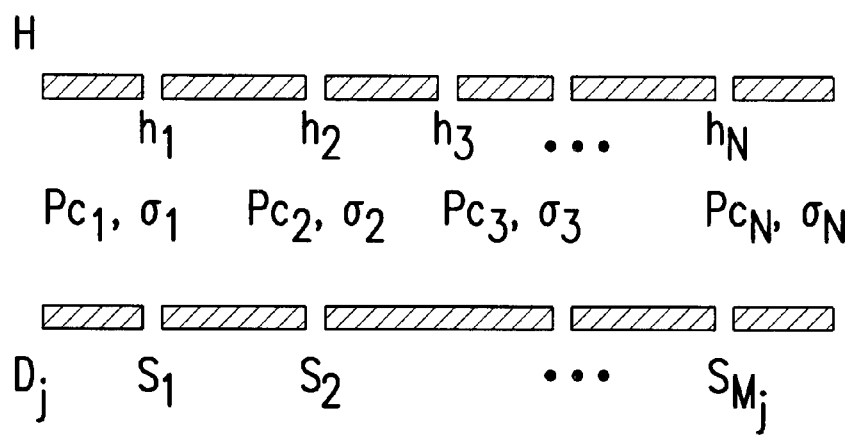
FIG. 3 is a graphic representation of a statistical model of a restriction map.

Thus our problem can be described as follows:

Given a collection of SMRM vectors, $$D_1, D_2, \ldots, D_m,$$

we need to compute a final vector $H = (h_1, h_2, \ldots, h_N)$ such that H is "consistent" with each $D_j$. Thus, H represents the correct restriction map and the $D_j$'s correspond to several "corrupted versions" of H. A graphical representation of H and one vector $D_j$ is depicted in FIG. 3.

We shall define such a general notion of "consistency" using a Bayesian approach which depends on the conditional probability that a data item $D_j$ can be present given that the correct restriction map for this particular clone is H.

In order to accurately model the prior distribution $\Pr[D|\mathcal{H}]$, we need to consider the following categories of errors in image data: 1) misidentification of spurious materials in the image as DNA, 2) identifying multiple DNA molecules as one, 3) identifying partial DNA molecules as complete, 4) errors in estimating sizes of DNA fragments, 5) incomplete digestion of DNA, 6) cuts visible at locations other than digest sites, and 7) unknown orientation of DNA molecule. Our prior distribution $\mathbf{P}[D|\mathcal{H}]$ is modeled as following:

- A molecule on the surface can be read from left to right or right to left. The uncertainty in orientation is modeled as Bernoulli processes, with the probability for each orientation being equal.
- The restrictions sites on the molecule are determined by a distribution induced by the underlying distribution of the four bases in the DNA. For example, we shall assume that the probability that a particular base (say, A) appears at a location i is independent of the other bases, though the probabilities are not necessarily identical.
- The false cuts appear on the molecule as a Poisson process. This is a consequence of the simplifying assumption that over a small region $\Delta h$ on the molecule, the $\Pr[\text{\# False cuts} = 1 \text{ over } \Delta h] = \lambda_f \Delta h$ and the $\Pr[\text{\#False cuts} \geq 2 \text{ over } \Delta h] = o(\Delta h)$.
- The fragment size (the size of the molecule between two cuts) is estimated with some loss of accuracy (dependent on the stretching of the molecule, fluorochrome attachments and the image processing algorithm). The measured size is assumed to be distributed as a Gaussian distribution.

The following notation will be used to describe the parameters of the independent processes responsible for the statistical structure of the data. Unless otherwise specified, the indices i, j and k are to have the following interpretation:

- The index i ranges from 1 to N and refers to cuts in the hypothesis.
- The index j ranges from 1 to M and refers to data items (i.e., molecules).
- The index k ranges from 1 to K and refers to a specific alignment of cuts in the hypothesis vs. data.

Now the main parameters of our Bayesian model are as follows:

- $p_{ci}$ = Probability that the ith sequence specific restriction site in the molecule will be visible as a cut.
- $\sigma_i$ = Standard deviation of the observed position of the ith cut when present and depends on the accuracy with which a fragment can be sized.
- $\lambda_f$ = Expected number of false-cuts per molecule observed. Since all sizes will be normalized by the molecule size, this will also be the false-cuts per unit length.
- $p_b$ = Probability that the data is invalid ("bad"). In this case, the data item is assumed to have no relation to the hypothesis being tested, and could be an unrelated piece of DNA or a partial molecule with a significant fraction of the DNA missing. The cut-sites (all false) on this data item are assumed to have been generated by a Poisson process with the expected number of cuts=$\lambda_n$. Note that the regular DNA model reduces to the "bad" DNA model for the degenerate situation when $p_{ci} \to 0$ and $\lambda_f \to \lambda_n$. As a result, "bad" DNA molecules cannot be disambiguated from regular DNA molecules if $p_{ci} \approx 0$. In practice, $p_{ci} > 0$ and $\lambda_n > \lambda_f$, and the degenerate case almost never occurs. Here the "bad" molecules are recognized by having a disproportionately large number of false cuts.
- $\lambda_n$ = Expected number of cuts per "bad" molecule.

B. Prior Distribution in the Hypotheses Space

Recall that by Bayes' rule $$Pr[\mathcal{H} | \mathcal{D}] = \frac{Pr[\mathcal{D} | \mathcal{H}] Pr(\mathcal{H})}{Pr[\mathcal{D}]}$$

Assuming that the prior distribution $\mathbf{Pr}\mathcal{H}$ is given in terms of just the number of restriction sites, based on the standard Poisson distribution, we wish to find the "most plausible" hypothesis $\mathcal{H}$ by maximizing $\Pr[\mathcal{H}|D]$.

In our case, $\mathcal{H}$ is simply the final map (a sequence of restriction sites, $h_1, h_2, \ldots h_N$) augmented by the auxiliary parameters such as $p_{ci}, \sigma_i, \lambda_f$, etc. When we compare a data item $D_j$ with respect to this hypothesis, we need to consider every possible way that $D_j$ could have been generated by $\mathcal{H}$. In particular we need to consider every possible alignment, where the kth alignment, $A_{jk}$, corresponds to a choice of the orientation for $D_j$ as well as identifying a cut on $D_j$ with a true restriction site on $\mathcal{H}$ or labeling the cut as a false cut. By $D^{(A_{jk})}{}_j$ [also abbreviated as $D^{(k)}{}_j$], we shall denote the "interpretation of the jth data item with respect to the alignment $A_{jk}$." Each alignment describes an independent process by which $D_j$ could have been generated from $\mathcal{H}$, and therefore the total probability distribution of $D_j$ is the sum of the probability distribution of all these alignments, plus the remaining possible derivations (invalid data).

As a consequence of the pairwise independence and the preceding discussion, we have the following:

$$Pr[\mathcal{D}|\mathcal{H}] = \sum_{j}^{M} Pr[D_j|\mathcal{H}],$$

where index j ranges over the data set, and $$Pr_j \equiv Pr[D_j|\mathcal{H}] = \frac{1}{2}\sum_{k} Pr[D_j^{(k)}|\mathcal{H}, \text{good}]Pr[\text{good}] + \frac{1}{2}\sum_{k} Pr[D_j^{(k)}|\mathcal{H}, \text{bad}]Pr[\text{bad}]$$

where index k ranges over the set of alignments.

In the preceding equation, $Pr[D^{(k)}_j|\mathcal{H} \text{ good}]$ (abbreviated, $Pr_{jk}$) is the probability distribution of model $D_j$ being derived from model $\mathcal{H}$ and corresponding to a particular alignment of cuts (denoted, $A_{jk}$). The set of alignments includes alignments for both orientations, hence each alignment has a prior probability of ½. If $D_j$ is bad, our model corresponds to $\mathcal{H}$ with $p_{ci} \to 0$ and $\lambda_f \to \lambda_n$. We shall often omit the qualifier "good" for the hypothesis $\mathcal{H}$ when it is clear from the context.

Figure 4:
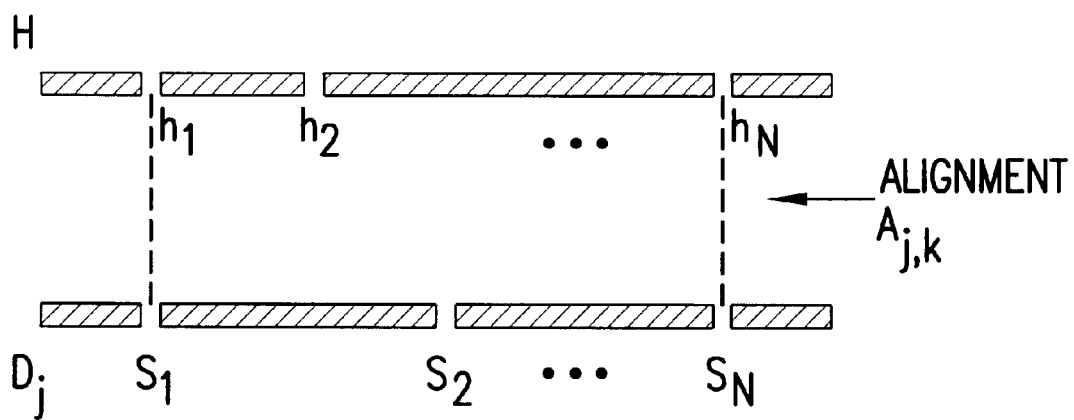
FIG. 4 is an example of the alignment detection.

Thus, in the example shown in FIG. 4, for a given hypothesis $\mathcal{H}$, the conditional probability distribution that the jth data item $D_j$ with respect to alignment $A_{jk}$ (i.e., $D^{(k)}_j$) could have occurred is given by the following formula:

$$Pr_{jk} = p_{c_1} \frac{e^{-(s_1-h_1)^2/2\sigma_1^2}}{\sqrt{2\pi}\,\sigma_1} \times (1-p_{c_2}) \times$$
$$\lambda_f e^{-\lambda_f} \times \cdots \times p_{c_N} \frac{e^{-(s_N-h_N)^2/2\sigma_N^2}}{\sqrt{2\pi}\,\sigma_N}.$$

In the most general case, we proceed as follows. Let

A≡N Number of cuts in the hypothesis $\mathcal{H}$.
$h_i$≡The ith cut location on $\mathcal{H}$.
$M_j$≡Number of cuts in the data $D_j$.
$K_j$≡Number of possible alignments of the data/evidence $D_j$ against the hypothesis $\mathcal{H}$ (or its reversal, the flipped alignment $\mathcal{H}^R$). $s_{ijk}$≡The cut location in $D_j$ matching the cut $h_i$ in $\mathcal{H}$, given the alignment $A_{jk}$. In case such a match occurs, this event is denoted by an indicator variable $m_{ijk}$ taking the value 1.
$m_{ijk}$≡An indicator variable, taking the value 1 if and only if the cut $s_{ijk}$ in $D_j$ matches a cut $h_i$ in the hypothesis $\mathcal{H}$, given the alignment $A_{jk}$. It takes the value 0, otherwise.
$F_{jk}$≡Number of false (non-matching) cuts in the data $D_j$ for alignment $A_{jk}$, tat do not match any cut in the hypothesis $\mathcal{H}$. Thus $$F_{jk} = M_j - \sum_{i=1}^{N} m_{ijk}$$

The number of missing cuts is thus $$\sum_{i=1}^{N}(1-m_{ijk}) = N - \sum_{i=1}^{N} m_{ijk}.$$

We may omit the indices j and k, if from the context it can be uniquely determined which data $D_j$ and alignment $A_{jk}$ are being referred to.

Note that a fixed alignment $A_{jk}$ can be uniquely described by marking the cuts on $D_j$ by the labels T (for true cut) and F (for false cut) and by further augmenting each true cut by the identity of the cut $h_i$ of the hypothesis $\mathcal{H}$. From this information, $m_{ijk}$, $s_{ijk}$, $F_{jk}$, etc. can all be uniquely determined. Let the cuts of $D_j$ be $(s_1, s_2, \ldots, s_{M_j})$. Let the event $E_i$ denote the situation that there is a cut in the infinitesimal interval $(s_i-\Delta x/2, s_i+\Delta x/2)$. Thus we have:

$$Pr[D_j^{(k)}|\mathcal{H}, \text{good}]\Delta x_1 \cdots \Delta x_{M_j} = Pr[D_j^{(k)}|\mathcal{H}, \text{good}](\Delta x)^{M_j}$$
$$= prob[E_1, \ldots, E_{M_j}, A_{jk}|\mathcal{H}, \text{good}]$$
$$= prob[E_1, \ldots, E_{M_j}, A_{jk}|m_{ijk}, M_j, \mathcal{H}, \text{good}] \times prob[m_{ijk}, M_j, \mathcal{H}, \text{good}]$$
$$= prob[E_1, A_{jk}|m_{ijk}, M_j, \mathcal{H}, \text{good}] \times prob[E_2, A_{jk}|E_1, m_{ijk}, M_j, \mathcal{H}, \text{good}] \times$$
$$\cdots \times prob[E_\alpha, A_{jk}|E_1, \ldots, E_{\alpha-1}, m_{ijk}, M_j, \mathcal{H}, \text{good}] \times \cdots \times$$
$$prob[E_{M_j}, A_{jk}|E_1, \ldots, E_{M_j-1}, m_{ijk}, M_j, \mathcal{H}, \text{good}] \times$$
$$prob[m_{ijk}, M_j|\mathcal{H}, \text{good}]$$

Note the following:

$$prob[m_{ijk}, M_j|\mathcal{H}, \text{good}] = \left[\prod_{i=1}^{N}(p_{c_i}, m_{ijk} + (1-p_{c_i})(1-m_{ijk}))\right] \times$$
$$e^{-\lambda_f}\lambda_f^{F_{jk}}/F_{jk}!$$
$$= \left[\prod_{i=1}^{N} p_{c_i}^{m_{ijk}}(1-p_{c_i})^{(1-m_{ijk})}\right] \times$$
$$e^{-\lambda_f}\lambda_f^{F_{jk}}/F_{jk}!$$

For the event $E_\alpha$ there are two possible situations to be considered:

(a) $s_\alpha$ is a false cut and the number of false cuts among $s_1, \ldots, s_{\alpha-1}$ is β. $prob[E_\alpha, A_{jk}|E_1, \ldots, E_{\alpha-1}, m_{ijk}, M_j, \mathcal{H}, \text{good}] = (F_{jk}-\beta)\Delta x$.

(b) $s_\alpha = s_{ijk}$ is a true cut and $h_i$ is the cut in $\mathcal{H}$ associated with it.

$$prob[E_\alpha, A_{jk}|E_1, \ldots, E_{\alpha-1}, m_{ijk}, M_j, \mathcal{H}, \text{good}] = \frac{e^{-(s_{ijk}-h_i)^2/2\sigma_i^2}}{\sqrt{2\pi}\,\sigma_i}\Delta x.$$

Thus, $$prob[E_1, \ldots, E_{M_j}, A_{jk} | m_{ijk}, M_j, \mathcal{H}, \text{good}] = \prod_{i=1}^{N} \left( \frac{e^{-(s_{ijk}-h_i)^2/2\sigma_i^2}}{\sqrt{2\pi}\, \sigma_i} \Delta x \right)^{m_{ijk}} \times$$

$$F_{jk}!(\Delta x)^{F_{jk}}$$

$$= F_{jk}! \prod_{i=1}^{N} \left( \frac{e^{-(s_{ijk}-h_i)^2/2\sigma_i^2}}{\sqrt{2\pi}\, 94_{z_i}} \right)^{m_{ijk}} (\Delta x)^{M_j}$$

Putting it all together:

$$Pr[D_j^{(k)} | \mathcal{H}, \text{good}] = \quad (1)$$

$$\left[ \prod_{i=1}^{N} \left( p_{c_i} \frac{e^{-(s_{ijk}-h_i)^2/2\sigma_i^2}}{\sqrt{2\pi}\, \sigma_i} \right)^{1-m_{ijk}} (1-p_{c_i})^{(1-m_{ijk})} \right] \times e^{-\lambda_f} \lambda_f^{F_{jk}}.$$

By an identical argument we see that the only alignments relevant for the bad molecules correspond to the situation when all cuts in $D_j$ are labeled false, and for each of two such alignments, $$Pr[D_j^{(k)} | \mathcal{H}, \text{bad}] = e^{-\lambda_n''} \lambda_n^{M_j}.$$

The log-likelihood can then be computed as follows:

$$\mathcal{L} \equiv \sum_j \log Pr[D_j | \mathcal{H}].$$

Thus, $$\mathcal{L} = \sum_j \log \left[ p_b e^{-\lambda_n \lambda_n^{M_j}} + \frac{(1-p_b)}{2} \sum_k Pr_{jk} \right]$$

$$= \sum_j \log[p_b e_j + (1-p_b)d_j]$$

where, by definition, $e_j \equiv e^{-\lambda_n \lambda_n^{M_j}}$, and $d_j \equiv \left( \sum_k Pr_{jk} \right) / 2.$ In the model, we shall use an extremely simple distribution on the prior distribution $\mathbf{Pr}[\mathcal{H}]$ that only depends on the number of restriction sites N and not any other parameters. Implicitly, we assume that all hypotheses with the same number of cuts are equi-probable, independent of the cut location.

Given a k-cutter enzyme (e.g., normally six-cutters like EcoR I in our case), the probability that it cuts at any specific site in a sufficiently long clone is given by $$p_e = \left(\frac{1}{4}\right)^k.$$

Thus if the clone is of length G bps we denote by $\lambda_e = G p_e$ (the expected number of restriction sites in the clone), then the probability that the clone has exactly N restriction cuts is given by $$prob[\text{\# restriction sites} = N \mid \text{enzymes,}$$

$$e \text{ and clone of length } G] \approx e^{-\lambda_e} \frac{\lambda_e^N}{N!}.$$

The preceding computation is based on the assumption that all four bases $\in \{A,T,C,G\}$ occur in the clone with equal probability ¼. However, as is known, the human genome is CG-poor (i.e., $\mathbf{Pr}[C]+\mathbf{P}[G]=0.32<\mathbf{P}[A]+\mathbf{P}[T]=0.68$). D. Barker, M. Schafer and R. White, "Restriction Sites Containing CpG Show a Higher Frequency of polymorphism in Human DNA," Cell, 36:131–138, (1984). A more realistic model can use a better estimation for $p_e$:

$$p_e = (0.16)^{\#CG}(0.34)^{\#AT},$$

where #CG denotes the number of C or G in the restriction sequence for the enzyme and, similarly, #AT denotes the number of A or T in the restriction sequence.

C. Local Search Algorithm

In order to find the most plausible restriction map, we shall optimize the cost function derived earlier, with respect to the following parameters:

Cut Sites=$h_1, h_2, \ldots, h_N$,
Cut Rates=$p_{c1}, p_{c2}, \ldots, p_{cN}$,
Std. Dev. of Cut Sites=$\sigma_1, \sigma_2, \ldots, \sigma_N$,
Auxiliary Parameters=$p_b, \lambda_f$ and $\lambda_n$.

Let us denote any of these parameters by $\theta$. Thus, we need to solve the equation $$\frac{\partial \mathcal{L}}{\partial \theta} = 0,$$

to find an extremal point of l with respect to the parameter $\theta$.

Case 1: $\theta = p_b$

Taking the first partial derivative, we get $$\frac{\partial \mathcal{L}}{\partial p_b} = \sum_j \frac{(e_j - d_j)}{p_b e_j + (1-p_b)d_j}. \quad (2)$$

Taking the second partial derivative, we get $$\frac{\partial^2 \mathcal{L}}{\partial p_b^2} = -\sum_j \frac{(e_j - d_j)^2}{[p_b e_j + (1-p_b)d_j]^2}. \quad (3)$$

Accordingly, l can now be easily optimized iteratively to estimate the best value of $p_b$, by means of the following applications of the Newton's equation:

$$p_b := p_b - \frac{\partial \mathcal{L}/\partial p_b}{\partial^2 \mathcal{L}/\partial p_b^2}.$$

Case 2: $\theta = \lambda_n$

This parameter is simply estimated to be the average number of cuts. Note that $$\frac{\partial \mathcal{L}}{\partial \lambda_n} = \sum_j \frac{p_b e_j (M_j/\lambda_n - 1)}{p_b e_j + (1-p_b) d_j}$$

should be zero at the local maxima. Thus a good approximation is obtained by taking $$\sum_j \left(\frac{M_j}{\lambda_n} - 1\right) \approx 0,$$

leading to the update rule $$\lambda_n := \frac{\sum_j M_j}{\sum_j 1} = \frac{\sum_j M_j}{\text{Total number of molecules}}.$$

Thus $\lambda_n$ is simply the average number of cuts per molecule.

Case 3: $\theta = h_i$, $p_{c_i}$, $\sigma_i (i=1, \ldots, N)$, or $\lambda_f$

Unlike in the previous two cases, these parameters are in the innermost section of our probability distribution expression and computing any of these gradients will turn out to be computationally comparable to evaluating the entire probability distribution.

In this case, $$\frac{\partial \mathcal{L}}{\partial \theta} = \sum_j \frac{1}{Pr_j} \left(\frac{1-p_b}{2} \sum_k Pr_{jk} \chi_{jk}(\theta)\right),$$

wehre $Pr_j \equiv Pr[D_j | \mathcal{H}]$ and here $$\chi_{jk}(\theta) = \left[\frac{F_{jk}}{\lambda_f} \frac{\partial \lambda_f}{\partial \theta} - \frac{\partial \lambda_f}{\partial \theta}\right] +$$

$$\sum_{i=1}^{N} \left[\frac{m_{ijk}}{p_{c_i}} \frac{\partial p_{c_i}}{\partial \theta} - \frac{1 - m_{ijk}}{1 - p_{c_i}} \frac{\partial p_{c_i}}{\partial \theta}\right] +$$

-continued $$\sum_{i=1}^{N} m_{ijk} \left[\frac{\partial}{\partial \theta}\left(\frac{-(s_{ijk} - h_i)^2}{2\sigma_i^2}\right) - \frac{1}{\sigma_i} \frac{\partial \sigma_i}{\partial \theta}\right].$$

For convenience, now define $$\pi_{jk} \equiv \left(\frac{1-p_b}{2}\right) \frac{Pr_{jk}}{Pr_j}$$

$\equiv$ Relative probability distribution of the alignment $A_{jk}$ for data item $D_j$. Thus, our earlier formula for $$\frac{\partial \mathcal{L}}{\partial \theta}$$

now simplifies to $$\frac{\partial \mathcal{L}}{\partial \theta} = \sum_j \sum_k \pi_{jk} \chi_{jk}(\theta).$$

Before examining the updating formula for each parameter optimization, we shall introduce the following notations for future use. The quantities defined below can be efficiently accumulated for a fixed value of the set of parameters.

$\Psi_{0i} \equiv \sum_j \sum_k \pi_{jk} m_{ijk}$ $\equiv$ Expected number of cuts matching $h_i$ $\Psi_{1i} \equiv \sum_j \sum_k \pi_{jk} m_{ijk} s_{ijk}$ $\equiv$ Sum of cut locations matching $h_i$ $\Psi_{2i} \equiv \sum_j \sum_k \pi_{jk} m_{ijk} s_{ijk}^2$ $\equiv$ Sum of square of cut locations matching $h_i$ $\mu_g \equiv \sum_j \sum_k \pi_{jk}$ $\equiv$ Expected number of "good" molecules $\gamma_g \equiv \sum_j \sum_k \pi_{jk} M_j$ $\equiv$ Expected number of cuts in "good" molecules We note here that the $\Psi$'s can all be computed efficiently using a simple updating rule that modifies the values with one data item $D_j$ (molecule) at a time. This rule can then be implemented using a Dynamic Programming recurrence equation (described later).

Case 3A: $\theta = h_i$ Note that $\theta \equiv h_i \Rightarrow$ $\chi_{jk}(h_i) = m_{ijk}(s_{ijk} - h_i)/\sigma_i^2 \Rightarrow$ $$\frac{\partial \mathcal{L}}{\partial h_i} = \sum_j \sum_k \pi_{jk} m_{ijk} (s_{ijk} - h_i)/\sigma_i^2.$$

Thus, $$\frac{\partial \mathcal{L}}{\partial h_i} = \frac{1}{\sigma_i^2} (\Psi_{1i} - h_i \Psi_{0i})$$

Although the $\Psi$'s depend on the location $h_i$, they vary rather slowly as a function of $h_i$. Hence a feasible update rule for $h_i$ is $$h_i := \frac{\Psi_{1i}}{\Psi_{0i}}. \tag{4}$$

Thus the updated value of $h_i$ is simply the "average expected value" of all the $s_{ijk}$'s that match the current value of $h_i$.

Case 3B: $\theta = p_{c_i}$ Note that $$\theta \equiv p_{c_i} \Rightarrow$$

$$\chi_{jk}(p_{c_i}) = \frac{m_{ijk}}{p_{c_i}} - \frac{1 - m_{ijk}}{1 - p_{c_i}} \Rightarrow$$

$$\frac{\partial \mathcal{L}}{\partial p_{c_i}} = \sum_j \sum_k \pi_{jk} \frac{m_{ijk}}{p_{c_i}} - \frac{1 - m_{ijk}}{1 - p_{c_i}}.$$

Thus, $$\frac{\partial \mathcal{L}}{\partial p_{c_i}} = \frac{\Psi_{0i}}{p_{c_i}} - \frac{\mu_g - \Psi_{0i}}{1 - p_{c_i}}.$$

Again, arguing as before, we have the following feasible update rule for $p_{c_i}$ $$p_{c_i} := \frac{\Psi_{0i}}{\mu_g}. \tag{5}$$

Thus $p_{c_i}$ is just the fraction of the good molecules that have a matching cut at the current value of $h_i$.

Case 3C: $\theta = \sigma_i$ Note that $$\theta \equiv \sigma_i \Rightarrow$$

$$\chi_{jk}(\sigma_i) = m_{ijk}\left(\frac{(s_{ijk} - h_i)^2}{\sigma_i^3} - \frac{1}{\sigma_i}\right) \Rightarrow$$

$$\frac{\partial \mathcal{L}}{\partial \sigma_i} = \sum_j \sum_k \pi_{jk} m_{ijk} \left(\frac{(s_{ijk} - h_i)^2}{\sigma_i^3} - \frac{1}{\sigma_i}\right).$$

Thus, $$\frac{\partial \mathcal{L}}{\partial \sigma_i} = \frac{1}{\sigma_i^3}(\Psi_{2i} - 2h_i \Psi_{1i} + h_i^2 \Psi_{0i} - \sigma_i^2 \Psi_{0i}).$$

Thus, we have the following feasible update rule for $\sigma_i^2$ $$\sigma_i^2 := \frac{(\Psi_{2i} - 2h_i \Psi_{1i} + h_i^2 \Psi_{0i})}{\Psi_{0i}}.$$

Using the estimate for $h_i$ (equation (4)), we have $$\sigma_i^2 := \frac{\Psi_{2i}}{\Psi_{0i}} - \left(\frac{\Psi_{1i}}{\Psi_{0i}}\right)^2. \tag{6}$$

This is simply the variance of all the $s_{ijk}$'s that match the current value of $h_i$.

Case 3D: $\theta = \lambda_f$ Note that $$\theta \equiv \lambda_f \Rightarrow$$

$$\chi_{jk}(\lambda_f) = \frac{F_{jk}}{\lambda_f} - 1 = \frac{M_j - \sum_i m_{ijk}}{\lambda_f} - 1 \Rightarrow$$

$$\frac{\partial \mathcal{L}}{\partial \lambda_f} = \sum_j \sum_k \pi_{jk} \left(\frac{M_j - \sum_i m_{ijk}}{\lambda_f} - 1\right)$$

$$= \frac{\gamma_g - \sum_i \Psi_{0i}}{\lambda_f} - \mu_g.$$

Thus, we have the following feasible update rule for $\lambda_f$ $$\lambda_f := \frac{\gamma_g}{\mu_g} - \sum_i \frac{\Psi_{0i}}{\mu_g}. \tag{7}$$

This is simply the average number of unmatched cuts per "good" molecule. (Note that the molecules are already normalized to unit length.)

Case 3E: $\theta = p_c = p_{c1} = \ldots = p_{cN}$ (Constrained) Note that $$\frac{\partial \mathcal{L}}{\partial p_c} = \sum_j \sum_k \sum_{i=1}^N \pi_{jk} \left(\frac{m_{ijk}}{p_c} - \frac{1 - m_{ijk}}{1 - p_c}\right)$$

Thus the update equation for this case is:

$$p_c := \frac{\sum_i \Psi_{0i}/N}{\mu_g}. \tag{8}$$

Case 3F: $\theta = \sigma = \sigma \ldots = \sigma_N$ (Constrained) Note that $$\frac{\partial \mathcal{L}}{\partial \sigma} = \sum_j \sum_k \sum_{i=1}^N \pi_{jk} m_{ijk} \left(\frac{(s_{ijk} - h_i)^2}{\sigma^3} - \frac{1}{\sigma}\right).$$

Thus the update equation for this case is:

$$\sigma^2 := \frac{\sum_i (\Psi_{2i} - \Psi_{1i}^2/\Psi_{0i})}{\sum_i \Psi_{0i}}. \tag{9}$$

D. Update Algorithm: Dynamic Programming

In each update step, we need to compute the new values of the parameters based on the old values of the parameters, which affect the "moment functions": $\Psi_{0i}$, $\Psi_{1i}$, $\Psi_{2i}$, $\mu_g$ and $\gamma_g$. For the ease of expressing the computation, we shall use additional auxiliary expressions as follows:

$$P_j \equiv \sum_k \left( \frac{Pr_{jk}}{e^{-\lambda_f}} \right)$$

$$W_{ij} \equiv \sum_k \left( \frac{Pr_{jk} m_{ijk}}{e^{-\lambda_f}} \right)$$

$$SUM_{ij} \equiv \sum_k \left( \frac{Pr_{jk} m_{ijk} s_{ijk}}{e^{-\lambda_f}} \right)$$

$$SQ_{ij} \equiv \sum_k \left( \frac{Pr_{jk} m_{ijk} s_{ijk}^2}{e^{-\lambda_f}} \right)$$

(10)

One motivation for this formulation is to avoid having to compute $e^{-\lambda_f}$ repeatedly, since this is a relatively expensive computation. Note that the original moment function can now be computed as follows:

$$Pr_j = \left(\frac{1-p_b}{2}\right) e^{-\lambda_f} \times P_j + p_b e_j$$

$$\Psi_{0i} = \left(\frac{1-p_b}{2}\right) e^{-\lambda_f} \sum_j \frac{W_{ij}}{Pr_j}$$

$$\Psi_{1i} = \left(\frac{1-p_b}{2}\right) e^{-\lambda_f} \sum_j \frac{SUM_{ij}}{Pr_j}$$

$$\Psi_{2i} = \left(\frac{1-p_b}{2}\right) e^{-\lambda_f} \sum_j \frac{SQ_{ij}}{Pr_j}$$

$$\mu_g = \left(\frac{1-p_b}{2}\right) e^{-\lambda_f} \sum_j \frac{P_j}{Pr_j}$$

$$\gamma_g = \left(\frac{1-p_b}{2}\right) e^{-\lambda_f} \sum_j \frac{M_j P_j}{Pr_j}$$

(11)

Finally, $$Pr[\mathcal{D} | \mathcal{H}] = \prod_j Pr_j.$$

The definitions for $P_j$, $W_{ij}$, $SUM_{ij}$ and $SQ_{ij}$ involve all alignments between each data element $D_j$ and the hypothesis $\mathcal{H}$. This number is easily seen to be exponential in the number of cuts N in the hypothesis $\mathcal{H}$, even if one excludes such physically impossible alignments as the ones involving cross-overs (i.e., alignments in which the order of cuts in $\mathcal{H}$ and $D_j$ are different). First, consider $P_j$:

$$P_j = \sum_k \left(\frac{Pr_{jk}}{e^{-\lambda_f}}\right)$$

$$= \sum_k \left\{ \prod_{i=1}^{N} \left( p_{c_i} \frac{e^{-(h_i - s_{ijk})^2/2\sigma_i^2}}{\sqrt{2\pi}\,\sigma_i} \right)^{m_{ijk}} \times \prod_{i=1}^{n}(1 - p_{c_i})^{1-m_{ijk}} \times \lambda_f^{F_{jk}} \right\}$$

Next we shall describe recurrence equations for computing the values for all alignments efficiently. The set of alignments computed are for the cuts $\{1, \ldots, M_j\}$ of $D_j$ mapped against the hypothesized cuts $\{1, \ldots, N\}$. We define the recurrence equations in terms of $$P_{q,r} \equiv P_j(s_q, \ldots, s_{M_j}, h_r, \ldots, h_N),$$

which is the probability density of all alignments for the simpler problem in which cuts $s_1, \ldots, s_{q-1}$ are missing in the data $D_j$ and the cuts $h_1, \ldots, h_{r-1}$ are missing in the hypothesis $\mathcal{H}$.

Then, clearly $$P_j \equiv P_{1,1}$$ (12)

$$P_{q,r} \equiv \lambda_f P_{q+1,r} + \sum_{t=r}^{N} P_{q+1,t+1} \left\{ \prod_{i=r}^{t-1}(1-p_{c_i}) \right\} p_{c_t} \frac{e^{-(h_t - s_q)^2/2\sigma_t^2}}{\sqrt{2\pi}\,\sigma_t},$$

This follows from a nested enumeration of all possible alignments. The recurrence terminates in $P_{M_j+1,r}$, which represents $P_j$ if all cuts in $D_j$ were missing and cuts $h_1, \ldots, h_{r-1}$ in $\mathcal{H}$ were missing:

$$P_{M_j,r} = \prod_{i=r}^{N}(1 - p_{c_i}).$$ (13)

where $1 \leq q \leq M_j$ and $1 \leq r \leq N+1$.

Thus the total number of terms $P_{q,r}$ to be computed is bounded from above by $(M_j+1)(N+1)$ where $M_j$ is the number of cuts in data molecule $D_j$ and N is the number of cuts in $\mathcal{H}$. Each term can be computed in descending order of q and r using equations (12) and (13). The time complexity associated with the computation of $P_{q,r}$ is $O(N-r)$ in terms of the arithmetic operations.

Note also that the equation (12) can be written in the following alternative form:

$$P_j \equiv P_{1,1}$$ (14)

$$P_{q,r} \equiv \lambda_f P_{q+1,r} + P_{q+1,r+1} p_{c_t} \frac{e^{-(h_t - s_q)^2/2\sigma_t^2}}{\sqrt{2\pi}\,\sigma_t} + (1 - p_{c_r})\{P_{q,r+1} - \lambda_f P_{q+1,r+1}\}$$

where $1 \leq q \leq M_j$ and $1 \leq r \leq N+1$.

Thus, by computing $P_{q,r}$ in descending order of r, only two new terms [and one new product $(1-p_{c_r})$ in equation (14)] need be to be computed for each $P_{q,r}$. With this modification, the overall time complexity reduces to $O(M_j N)$.

The complexity can be further reduced by taking advantage of the fact that the exponential term is negligibly small unless $h_i$ and $s_q$ are sufficiently close (e.g., $|h_t - s_q| \leq 3\,\sigma_t$). For any given value of q, only a small number of $h_i$ will be close to $s_q$. For a desired finite precision only a small constant fraction of $h_t$'s will be sufficiently close to $s_q$ to require that the term with the exponent be included in the summation (in practice, even a precision of $10^{-10}$ will only require 3–5 terms to be included with a around 1%).

Note however that even with this optimization in the computation for equation (12), the computation of $P_{q,r}$ achieves no asymptotic improvement in the time complexity, since $P_{q,r}$ with consecutive r can be computed with only two new terms, as noted earlier. However, for any given q, only for a few r values are both of these additional terms non-negligible. The range of r values (say, between $r_{min}$ and $r_{max}$) for which the new terms with $e^{-(hr-sq)^2/2\sigma'^2}$ are significant can be precomputed in a table indexed by $q=1, \ldots, M_j$. For $r>r_{max}$ all terms in the summation are negligible. For $r<r_{min}$ the new exponential term referred to previously is negligible. In both cases, the expression for $P_{q,r}$ can be simplified:

$$P_{q,r} = \begin{cases} \lambda_f P_{q+1,r}, & \text{if } r > r_{max}[q]; \\ \lambda_f P_{q+1,r} + (1-p_{c_r})(P_{q,r+1} - \lambda_f P_{q+1,r+1}), & \text{if } r < r_{min}[q]. \end{cases} \quad (15)$$

Figure 5:
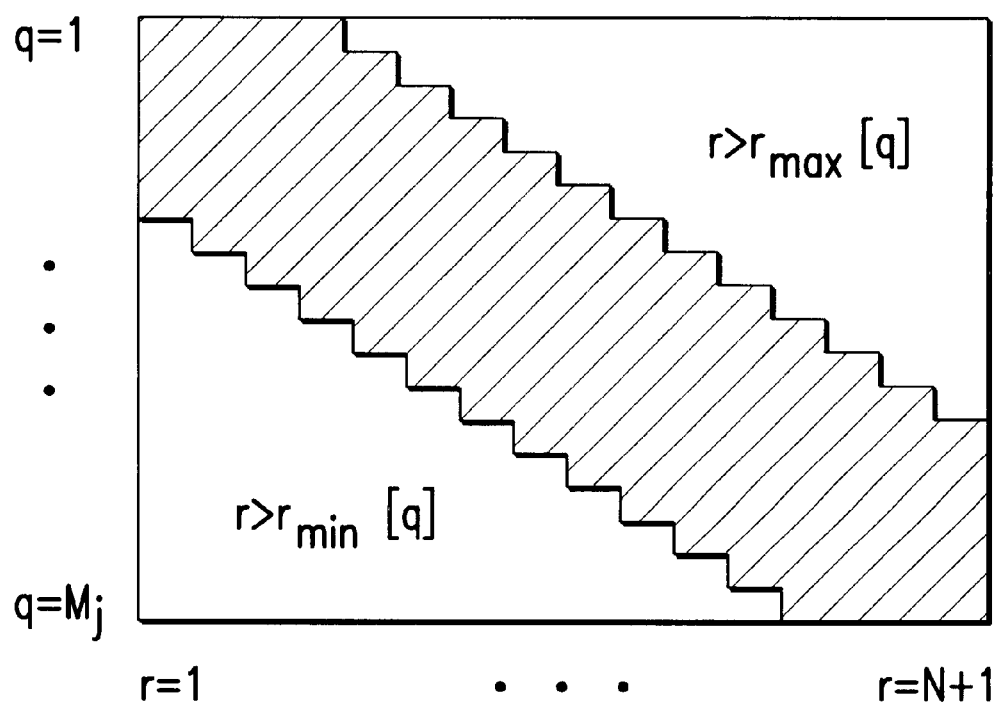
FIG. 5 illustrates a variable block diagonal matrix for the dynamic programming process.

Since both $r_{min}[q]$ and $r_{max}[q]$ are monotonically nondecreasing functions of q, the (q,r) space divides as shown in FIG. 5. Of course, the block diagonal pattern need not be as regular as shown and will differ for each data molecule $D_j$.

Note again that our ultimate object is to compute $P_{1,1}$. Terms $P_{q,r+1}$ with $r>r_{max}[q]$, cannot influence any term $P_{q'r'}$ with $r' \leq r$ (see equation (12)). Therefore, any term $P_{q,r+1}$ with $r>r_{max}[q]$ cannot influence $P_{1,1}$ as is readily seen by a straightforward inductive argument. Therefore, all such terms need not be computed at all.

For $r<r_{min}[q]$, these terms are required but need not be computed since they always satisfy the following identity:

$$P_{q,r} = (1-p_{cr})P_{q,r+1}, \quad r<r_{min}[q].$$

This follows from equations (13) and (15) by induction on q. These terms can then be generated on demand when the normal recurrence (equation (12)) is computed and whenever a term $P_{q+1,r}$ is required for which $r<r_{min}[q+1]$, provided terms are processed in descending order of r.

Thus, the effective complexity of the algorithm is $O(M_j(r_{max}-r_{min}+2))$. Since $r_{max}-r_{min}+2$ is proportional for a given precision to $[F(\sigma N+1)]$, (where $\sigma$ is an upper bound on all the $\sigma_t$ values) we see that the time complexity for a single molecule $D_j$ is $O(\sigma M_j N)$. Summing over all molecules $D_j$ the total time complexity is $O(\sigma MN)$, where $M=\Sigma_j M_j$. The space complexity is trivially bounded by $O(M_{max}N)$ where $M_{max}=\max_j M_j$.

Essentially the same recurrence equations can be used to compute $W_{ij}$, $SUM_{ij}$ and $SQ_{ij}$, since these 3N quantities sum up the same probability distribution $\Pr_{jk}$ weighted by $m_{ijk}$, $m_{ijk}s_{ijk}$ or $m_{ijk}s^2_{ijk}$, respectively. The difference is that the termination of the recurrence (cf equation (13)) is simply $P_{M_j+1,r}=0$, whereas the basic recurrence equation (cf equation(12)) contains an additional term corresponding to the $m_{ijk}$ times the corresponding term in the recurrence equation. For example:

$$SUM_{ij} \equiv SUM_{i,1,1} \quad (16)$$

$$SUM_{i,q,r} \equiv \lambda_f SUM_{i,q+1,r} + \sum_{t=r}^{N} SUM_{i,q+1,t+1} \left\{ \prod_{j=r}^{t-1}(1-p_{c_j}) \right\}$$

$$p_{c_i} \frac{e^{-(h_t-s_q)^2/2\sigma_t^2}}{\sqrt{2\pi}\,\sigma_i} + I_{i\geq r}s_q P_{q+1,i+1} \left\{ \prod_{j=r}^{i-1}(1-p_{c_j}) \right\}$$

$$p_{c_i} \frac{e^{(h_i-s_q)^2/2\sigma_i^2}}{\sqrt{2\pi}\,\sigma_i},$$

where $1 \leq q \leq M_j$ and $1 \leq r \leq N+1$.

Note that the new term is only present and as before need only be computed if the corresponding exponent is significant, i.e., i lies between $r_{min}[q]$ and $r_{max}[q]$. This term is the only nonzero input term in the recurrence since the terminal terms are zero. This recurrence is most easily derived by noting (from equations (1) and (10)) that the sum of products form of $SUM_{ij}$ can be derived from that of $P_j$ by multiplying each product term with $h_i-s_q$ in any exponent by $s_q$, and deleting any term without $h_i$ in the exponent. Since each product term contains at most one exponent with $h_i$, this transformation can also be applied to the recurrence form for $P_j$ (equation (12)), which is just a different factorization of the original sum of products form. The result is equation (16). The corresponding derivation for $W_{ij}$ and $SQ_{ij}$ is the same except that the $s_q$ is replaced by 1 or $s_q^2$ respectively. If the recurrences for these 3N quantities are computed in parallel with the probability distribution $P_j$, the cost of the extra term is negligible, so the overall cost of computing both the probability distribution $P_j$ and its gradients is $O(\sigma MN^2)$. The cost of conversion equations (11) is also negligible in comparison. Moreover this can be implemented as a vectorized version of the basic recurrence with vector size 3N+1 to take advantage of either vector processors or superscalar pipelined processors. We note in passing that if 3N is significantly greater than the average width $\sigma M$ of the dynamic programming block diagonal matrix shown in FIG. 3, then a standard strength reduction can be applied to the vectorized recurrence equations trading the 3N vector size for a $\sigma N+1$ vector size and resulting in an alternate complexity of $O(\sigma^2 MN^2)$. Note that the gradient must be computed a number of times (typically 10–20 times) for the parameters to converge to a local maximum and the gain is significant only when $\sigma<<1$.

E. Global Search Algorithm

Recall that our prior distribution $\Pr[D|\mathcal{H}]$ is multimodal and the local search based on the gradients by itself cannot evaluate the best value of the parameters. Instead, we must rely on some sampling method to find points in the parameter space. that are likely to be near the global maxima. Furthermore, examining the parameter space, we notice that the parameters corresponding to the number and locations of restriction sites present the largest amount of multimodal variability and hence the sampling may be restricted to just $\bar{h}=(N; h_1, h_2, \ldots, h_N)$. The conditional observation probability distribution $\Pr[D|\mathcal{H}]$ can be evaluated pointwise in time $O(\sigma MN)$ and the nearest local maxima located in time $O(\sigma MN^2)$, though there is no efficient way to sample all local maxima exhaustively.

Thus, our global search algorithm will proceed as follows: we shall first generate a set of samples $(\bar{h}_1, \bar{h}_2, \bar{h}_3, \ldots)$; these points are then used to begin a gradient search for the nearest maxima and provide hypotheses $(\mathcal{H}_1, \mathcal{H}_2, \mathcal{H}_3, \ldots)$; the hypotheses are then ranked in terms of their posterior probability distribution $\Pr[\mathcal{H}|D]$ (whose relative values also lead to the quality measure for each hypothesis) and the one (or more) leading to maximal posterior probability distribution is presented as the final answer.

However, even after restricting the sampling space, the high dimension of the space makes the sampling task daunting. Even if the space is discretized (for instance, each $h_i \in \{0, 1/200, \ldots, j/200, \ldots, 1\}$), there are still far too many sample points ($200^N$) even for a small number of cuts (say, N=8). However, the efficiency can be improved if we accept an approximate solution.

We use approximate Bayesian probability distributions in conjunction with a branch and bound algorithm to reject a large fraction of the samples without further local analysis.

For the present the parameter N is searched in strictly ascending order. This means one first evaluates the (single) map with no cuts, then applies global and gradient search to locate the best map with 1 cut, then the best map with 2 cuts etc. One continues until the score of the best map of N cuts is significantly worse than the best map of 0 ... N-1 cuts.

The global search for a particular N uses an approximate Bayesian probability distribution with a scoring function that is amenable to an efficient branch-and-bound search. Observe that obtaining good scores for some molecule $D_j$ basically requires that as many cut locations $s_{ij}, \ldots, s_{Mjj}$ as possible must line up close to $h_1, h_2, \ldots, h_N$ in one of the two orientations. This means that any subset of the true map $h_1, h_2, \ldots, h_m$ (m<N) will score better than most other maps of size m, assuming that the digestion rate is equal ($p_c = p_{ci} = \ldots = p_{cN}$). Note that for physical reasons, the variation among the digestion rates is quite small; thus, our assumption is valid and permits us to explicitly constrain these parameters to be the same. For example, if ($h_1, h_2, \ldots, h_N$) is the correct map, one expects maps with single cuts located at [$h_i$] ($1 \leq i \leq N$) to score about equally well in terms of the Bayesian probability distribution. Similarly, maps with two cuts located at pairs of [$h_i, h_j$] ($1 \leq i < j \leq N$) score about equally well and better than arbitrarily chosen two cut maps. Furthermore, the pair-cut probability distribution are more robust than the single cut probability distribution with respect to the presence of false cuts, hence, less likely to score maps with cuts in other than the correct locations. Hence an approximate score function used for a map ($h_1, h_2, \ldots, h_N$) is the smallest probability distribution for any pair map [$h_i, h_j$] which is a subset of ($h_1, h_2, \ldots, h_N$). These pair map probability distribution can be precomputed for every possible pair ([$h_i, h_j$]) if $h_i, h_j$ are forced to have only K values along some finite sized grid, for example at exact multiples of ½% of the total molecule length for K=200. The pair map probability distribution can then be expressed in the form of a complete undirected graph, with K nodes corresponding to possible locations, and each edge between node i to j having an edge value equal to the precomputed pair map probability distribution of [$h_i, h_j$]. A candidate map ($h_1, h_2, \ldots, h_N$) corresponds to a clique of size N in the graph, and its approximate score corresponds to the smallest edge weight in the clique.

In general, the clique problem (for instance, with binary edge weights) is NP-complete and may not result in any asymptotic speedup over the exhaustive search. However, for our problem effective branch-and-bound search heuristics can be devised. Consider first the problem of finding just the best clique. We can devise two bounds that can eliminate much of the search space for the best clique:

The score of any edge of a clique is an upper bound on the score of that clique. If the previous best clique found during a search has a better (higher) score than the score of some edge, all cliques that include this edge can be ruled out.

For each node in the graph, one can precompute the score of the best edge that includes this node. If the previous best clique found during a search has a better (higher) score than this node score, all cliques that include this node can be ruled out.

As with all branch-and-bound heuristics, the effectiveness depends on quickly finding some good solutions, in this case cliques with good scores. We have found that an effective way is to sort all K nodes by the Bayesian scores of the corresponding single cut map. In other words, we first try nodes that correspond to restriction site locations that have a high observed cut rate in some orientation of the molecules. Also the nodes corresponding to cut sites of the best overall map so far (with fewer than N cut sites) are tried first.

For data consisting of a few hundred molecules, the branch-and-bound heuristics allows exhaustive search in under a minute on a Sparc System 20 with $N \leq 7$ (with K=200). For N>7, a simple step wise search procedure that searches for the best map ($h_1, h_2, \ldots, h_n$) by fixing N-7 nodes based on the previous best map, works well. The N-7 nodes selected are the optimal with respect to a simple metric, for instance, the nodes with the smallest standard error (i.e., ratio of standard deviation to square root of sample size).

Next, the global search is modified to save the best B (typically 8000) cliques of each size and then the exact Bayesian probability distribution is evaluated at each of these B locations, adding reasonable values for parameters other than (N; $h_1, \ldots, h_N$). These parameters can be taken from the previous best map, or by using some prior values if no previous best map is available. For some best scoring subset (typically 32–64) of these maps gradient search is used to locate the nearest maxima (and also accurate estimates for all parameters), and the best scoring maxima is used as the final estimate for the global maxima for the current value of N.

The branch-and-bound heuristics was modified to find the best B cliques, by maintaining the best B cliques (found so far) in a priority queue (with an ordering based on the approximate score).

F. A Quality Measure for the Best Map

As a quality measure for the best map, we use the estimated probability of the dominant mode (peak) of the posterior probability distribution. This could be computed by integrating the probability distribution over a small neighborhood of the peak (computed in the parameter space). Our cost function corresponds to a constant multiple of the posterior probability distribution, as we do not explicitly normalize the cost function by dividing by a denominator corresponding to the integral of the cost over the entire parameter space. To compute the quality measure we make the following simplifying assumption: "All peaks are sharp and the integral of the cost function over a neighborhood where the cost value is larger than a specific amount is proportional to the peak distribution." Also if we know the N most dominant peaks (typically N=64), we can approximate the integral over all space, by the integral over the N neighborhoods of these peaks. Thus we estimate our quality measure for the best map by the ratio of the value assigned to it (the integral of the cost function in a small neighborhood around it) to the sum of the values assigned to the N best peaks. This, of course, simplifies the computation while producing a rather good estimate. To take into account the sampling errors (when the number of molecules is small) we penalize (reduce) the distribution of the best map by an estimate of the sampling error. This approach makes the computed quality measure somewhat pessimistic but provides a lower bound.

As will be apparent to those skilled in the art, numerous modifications may be made to the specific embodiment of the invention described above that are within the spirit and scope of the invention.

What is claimed is:

1. A process for constructing an ordered restriction map based on data obtained from individual DNA molecules digested into fragments by restriction enzymes, comprising the steps of:

(a) modeling from the data obtained from each individual DNA molecule a restriction map in the form of a vector;

(b) for each such restriction map, finding a candidate restriction map, hereinafter referred to as a hypothesis map, which is locally most likely to be the true restriction map; and (c) ranking the individual hypothesis maps according to their likelihood of correctness.

2. The process according to claim 1 further comprising the step of choosing the most likely hypothesis map as the correct answer.

3. A process for constructing an ordered restriction map based on data obtained from individual DNA molecules digested into fragments by restriction enzymes, comprising the steps of:

(a) cutting a DNA molecule and its clones into fragments through the use of restriction enzymes;

(b) modeling from the data obtained from said fragments a restriction map in the form of a vector of fragment lengths;

(c) from many such restriction maps, finding a consensus ordered restriction map (hypothesis map), which is locally most likely to be the true restriction map, and assigning a confidence value; and (d) ranking the individual hypothesis maps according to their likelihood of correctness.

4. The process according to claim 3 further comprising the step of choosing the most likely hypothesis map as the correct answer.

5. A process for constructing an ordered restriction map based on data obtained from individual DNA molecules digested into fragments by restriction enzymes, comprising the steps of:

(a) cutting a DNA molecule and its clones into fragments through the use of restriction enzymes;

(b) modeling from the data obtained from said fragments a restriction map in the form of a vector of fragment lengths;

(c) from many such restriction maps, using a Bayesian inference method to find a consensus ordered restriction map (hypothesis map), which is locally most likely to be the true restriction map, and assigning a confidence value; and (d) ranking the individual hypothesis maps according to their likelihood of correctness.

6. A process for constructing an ordered restriction map based on data obtained from individual DNA molecules digested into fragments by restriction enzymes, comprising the steps of:

(a) cutting a DNA molecule and its clones into fragments through the use of restriction enzymes;

(b) storing data sets obtained from said fragments;

(c) making several guesses about the number of cuts, position of the cuts, digestion rate, contamination rate, and sizing error of the DNA molecules; and (d) for each such guess (hypothesis), computing how plausible it is that said data sets are consistent with that particular hypothesis.

7. The process of claim 6, wherein the process stops when it finds the most plausible hypothesis.

8. The process of claim 6, wherein said step of computing how plausible it is that said data sets are consistent with a particular hypothesis is performed using Bayesian analysis.

9. The process of claim 7, wherein gradient methods are used to determine which hypothesis is most plausible.

10. A process for constructing an ordered restriction map based on data obtained from individual DNA molecules digested into fragments by restriction enzymes, comprising the steps of:

(a) modeling from the data obtained from each individual DNA molecule a restriction map in the form of a vector;

(b) for each such restriction map, using Bayes' rule to find a candidate restriction map, hereinafter referred to as a hypothesis map, that is locally most likely to be the true restriction map; and (c) ranking the individual hypothesis maps according to their likelihood of correctness.

11. The process according to claim 10 further comprising the step of choosing the most likely hypothesis map as the correct answer.

12. The process according to claim 5 wherein an uncertainty in orientation of the molecule is modeled as a Bernoulli process.

13. The process according to claim 5 wherein the probability that a particular base appears at a location i is assumed to be independent of the other bases.

14. The process according to claim 5 wherein false cuts are modeled as a Poisson process.

15. The process according to claim 5 wherein for each k-th fragment, measured sizes of the fragments are assumed to be Gaussian distributed.

16. The process according to claim 5 wherein the step of searching the space of plausible hypotheses is made more computationally efficient through the use of a branch-and-bound search.

17. The process according to claim 5 wherein the most likely estimate is determined using an estimated probability of the dominant peak of the posterior probability distribution.

18. The process of claim 8, wherein the process stops when it finds the most plausible hypothesis.

19. The process of claim 8, wherein gradient and global search techniques are used to determine which hypothesis is most plausible.

* * * * *